US012776397B2

(12) United States Patent
Ramde et al.

(10) Patent No.: US 12,776,397 B2
(45) Date of Patent: Oct. 27, 2026

(54) PERSISTENT VERIFIABLE HEALTHCARE IDENTITY AND DATA OWNERSHIP

(71) Applicant: Datacurve, Inc., Los Altos, CA (US)

(72) Inventors: Rakesh Ramde, Los Altos, CA (US); Amanjyot Singh Johar, Sunnyvale, CA (US)

(73) Assignee: Datacurve, Inc., Los Altos, CA (US)

( * ) Notice: Subject to any disclaimer, the term of this patent is extended or adjusted under 35 U.S.C. 154(b) by 4 days.

(21) Appl. No.: 18/669,138

(22) Filed: May 20, 2024

(65) Prior Publication Data

US 2024/0420812 A1 Dec. 19, 2024

Related U.S. Application Data

(60) Provisional application No. 63/467,726, filed on May 19, 2023.

(51) Int. Cl.
*G16H 10/60* (2018.01)
*G16H 10/20* (2018.01)

(52) U.S. Cl.
CPC ............ *G16H 10/60* (2018.01); *G16H 10/20* (2018.01)

(58) Field of Classification Search
None
See application file for complete search history.

(56) References Cited

U.S. PATENT DOCUMENTS

2022/0139566 A1* 5/2022 Gardina ................ G16H 50/20 705/2
2022/0406419 A1* 12/2022 Kruger .................. G16H 10/60
2023/0268040 A1* 8/2023 Cordonnier ........... G16H 10/20 705/3
2024/0338680 A1* 10/2024 Witchey ............ G06Q 20/3672
2025/0131994 A1* 4/2025 Gross .................... G16H 20/00

FOREIGN PATENT DOCUMENTS

WO WO-2023159236 A1 * 8/2023 ............ G06T 13/80

OTHER PUBLICATIONS

Rai, S., et al., "Blockchain-based NFT for Healthcare System", 2023 IEEE 12th International Conference on Communication Systems and Network Technologies (CSNT). (Year: 2023).*

* cited by examiner

*Primary Examiner* — Clay C Lee
(74) *Attorney, Agent, or Firm* — Law Office of Dorian Cartwright; Dorian Cartwright

(57) ABSTRACT

Health information about an individual patient is collected from public and private systems into an electronic patient record. Health records can also be collected and maintained for clinical trial purposes. The records are represented as NFTs stored on a blockchain and securely exchanged in compliance with privacy, authentication, and healthcare data protocols.

17 Claims, 9 Drawing Sheets

800

PERSISTENT VERIFIABLE HEALTHCARE IDENTITY AND DATA OWNERSHIP

CROSS-REFERENCE TO RELATED APPLICATIONS

The invention claims priority under 35 USC 119(e) to 63/467,726, entitled NFT HEALTH RECORDS, and filed May 19, 2023, by Ramde et al., the contents of which are hereby incorporated in its entirety.

FIELD OF THE INVENTION

The invention relates generally to computer networks and computer software, and more specifically, to tracking and securely exchanging health records using NFTs.

BACKGROUND

Electronic health records for patients present a complicated task of accurately compiling information that must be kept private in view of local and federal regulations. Patients often change health providers and require specialized health services that need to access these electronic health records.

Health records have traditionally been paper-based and managed by healthcare providers. Electronic Medical Records (EMRs) have become increasingly popular in recent years due to their ability to improve healthcare delivery, reduce costs, and improve patient outcomes. EMRs are electronic versions of medical charts that contain patient information, including medical history, medications, allergies, and test results. EMRs have been widely adopted in the healthcare industry due to their potential to improve healthcare delivery, reduce costs, and improve patient outcomes.

However, these systems have their inefficiencies, including their lack of interoperability and susceptibility to data breaches. Interoperability refers to the ability of different systems to communicate with each other, share data, and work together seamlessly. However, EMRs are often unable to communicate with each other, resulting in difficulty sharing patient data across different providers and healthcare institutions. This lack of interoperability can lead to delays in patient care, duplication of tests, and other inefficiencies that can compromise patient outcomes. EMRs have also been known to be susceptible to data breaches and cyberattacks, compromising patient privacy and security. These systems often store large amounts of sensitive patient data, making them attractive targets for hackers. EMRs can also be vulnerable to human error, such as employees mistakenly sharing patient information with unauthorized parties or falling victim to phishing scams. Furthermore, EMRs can be challenging to use for healthcare providers, leading to user dissatisfaction and decreased productivity. The systems often have complex interfaces and require extensive training to use effectively, which can be time-consuming and costly. EMRs can also be prone to errors, such as incorrect data entry or misinterpretation of medical information. Blockchain-based health records offer a promising solution to these issues, with increased security, interoperability, and patient control.

Within the healthcare ecosystem, and particularly with respect to data and records, a similar problem exists with clinical trials which are also inefficient, opaque, and lack security measures for their processes as far as the data collected therein is concerned. The use of blockchain in clinical trials can help to address several issues such as data privacy, data integrity, and data sharing. By leveraging blockchain, clinical trial data can be securely stored and shared among authorized parties in a way that is transparent and tamper-proof. This can help in reducing both potential errors as well as fraud.

Today it is challenging for various caregivers to be connected to the necessary elements of the patient's health history. Patient data is fragmented across various providers, their EMR systems as well as patient's own electronic devices such as health and fitness trackers. These do not integrate well together, and even if a caregiver were to access this data set, there are questions about its authenticity, urgency and importance related to the patient's health at any given time.

Therefore, what is needed is a robust technique for tracking and exchanging health records using NFTs.

SUMMARY

To meet the above-described needs, methods, computer program products, and systems for tracking and exchanging health records using NFTs.

In one embodiment, biometric authentication data is collected and stored in association with private keys for a user wallet. When a user attempts to access an NET or other aspects of the wallet, biometric data is collected prior to release. Once authenticated, wallet transactions are completed.

Advantageously, electronic health records for patents are more reliable and secure.

BRIEF DESCRIPTION OF THE DRAWINGS

In the following drawings, like reference numbers are used to refer to like elements. Although the following figures depict various examples of the invention, the invention is not limited to the examples depicted in the figures.

DETAILED DESCRIPTION

Methods, computer program products, and systems for tracking and exchanging health records using NFTs. One of ordinary skill in the art will recognize many alternative embodiments that are not explicitly listed based on the following disclosure.

I. Systems for NFT Health Records (FIGS. 1-6)

Figure 1:
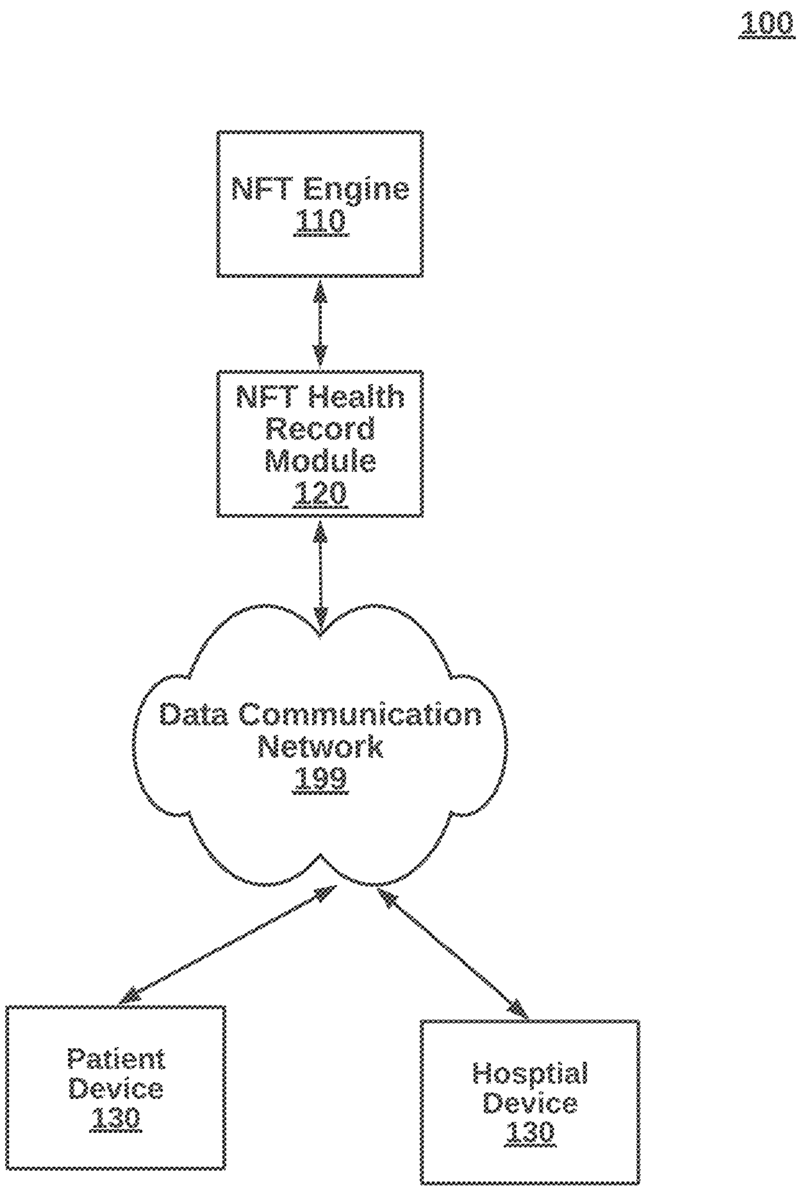
FIG. 1 is a high-level block diagram illustrating a system for tracking and exchanging health records using NFTs, according to an embodiment.

FIG. 1 is a high-level block diagram illustrating a system 100 for tracking and exchanging health records using NFTs, according to one embodiment. The system 100 includes an NFT engine 110, an NFT health record module 120 interacting over a data communication network 199 with a patient device 130 and hospital device 140, as users of the system 100. In one embodiment, the NFT engine 110 and the location transaction module 120 are integrated into a single physical device, and in another embodiment, communicate across the data communication network 199. Many other variations are possible.

Fungible cryptographic tokens are known. For example, one type of fungible token format is the well-known ERC-20 token. Non-fungible cryptographic tokens (NFTs) are known. For example, one type of NFT format is an ERC-721 token. Both are operable with an Ethereum virtual machine (EVM). While the token formats are known, each token can be configured to create unique functionality, unique expressions, or other unique aspects of the token. An NFT is a cryptographic token that represents ownership or other rights of a designated asset, e.g., a digital file or other assets associated with the token. Typically, the digital file or other asset is referenced in metadata in the token definition.

Token creation (e.g., minting) and transactions are typically handled via "smart contracts" and a blockchain (e.g., the Ethereum blockchain) or other distributed ledger technology. NFTs are minted according to known token minting protocols, but each can be configured with their own parameters to create uniqueness between the tokens. With some tokens, the token may be minted on demand when the token creator decides to mint the token. Some fungible tokens are minted and initially allocated via an initial coin offering. Some tokens are "pre-mined" and subsequently allocated. For example, once minted, an NFT is typically offered for sale or acquisition via an NFT marketplace or other token sale platform.

The existing token minting and sale process suffers from various technical drawbacks and limitations. For example, conventional "smart contracts" have numerous advantages but are limited in that typically they can operate only on the data contained inside the nodes of the blockchain on which they run. This makes them like a self-contained system, closed to external sources. This can be problematic when external data is needed to satisfy conditions of the smart contract.

In one embodiment, the NFT engine 110 mints and allocates tokens based on location-triggered events and providing access to token-gated content in response to a user satisfying specified token criteria. For example, minting a healthcare record every time a new patient report is generated. The credit may also be minted at any arbitrary time, or during a patient visit or a telemedicine session. Records may also be combined together or fractionated as they are shared across multiple caregivers and the compliance or regulatory terms may require for their custody purposes. Data triggered events can be monitored and anticipated via various mechanisms, such as, lab reports from Laboratory Information Systems (LIS), Radiology Information Systems (RIS), Pharmacy Information systems, Insurance information, and patient portals that aggregate these separate pieces of information. Other sources of data can also include information from workout equipment with Internet of things (IoT) devices, health sensors, analytics platforms, machine learning models that can analyze data and trigger events based on such analysis, or financial data to trigger a minting of a healthcare record as an NFT. Minting of health records can be triggered by non healthcare data such as an emergency response, social media posts, sentiment data analysis, or location based data analysis etc. For example, some NFTs can be based on physical activity or workout data such as a bike ride that may also track the bike route for the purpose deriving distance traveled, or elevation gains etc.

Other ways of minting the tokens for health records can include embedding into an existing EMR systems, where the minting system can connect to the various databases that monitor and track a patient's health. Health records can be made available as an add on for customers of cloud computing platforms. The NFTs can be minted in accordance with a hospital's policies on record keeping and sharing.

A token minting system for EMR or clinical trials application can be part of a laboratory, or a medical tests vendor, or any other web or mobile application. For example, the NFTs can be minted in accordance with a data access and sharing program of the platform, or integrations between various providers, or for any other tracking, or operational objectives. A standalone application such as a marketplace for health data can match buyers and sellers of such information. For example, many people may be interested in sharing their medical records for research or monetization purposes and getting compensated for it.

By using a blockchain-based system and NFTs for EMRs, patients can have more control over their own medical records and could grant access to healthcare providers as needed. The decentralized nature of blockchain could also make it more difficult for unauthorized individuals to access or tamper with medical records. Moreover, blockchain-based EMRs could facilitate data sharing between different healthcare providers and organizations, helping to improve care coordination and reduce medical errors. Additionally, the use of smart contracts on a blockchain could potentially automate various aspects of healthcare, such as insurance claims processing or medication tracking.

By using blockchain based systems for cataloging clinical trials from defining the scope to patient recruitment, administering double blinded studies, to recording relevant patient, provider, and drug data for control and test populations, to outcomes of the trials, the process inefficiencies can be greatly reduced. This will also result in a reduction in errors and fraud as the results from the clinical trials make their way into commercial drugs. The following are some advantages of doing so:

a. Increased transparency: A blockchain-based system can provide a secure and transparent platform for recording and sharing clinical trial data, which can improve transparency and trust between different stakeholders, such as patients, researchers, and regulators. Enhanced data security: Blockchain uses encryption and a decentralized architecture to secure clinical trial data against hacking, tampering, and other forms of cyber attacks, which can help to protect patient privacy and ensure data integrity.

b. Improved efficiency: Blockchain can automate certain aspects of clinical trial management, such as data collection, consent management, and payment processing, which can help to reduce the time and costs associated with clinical trials.

c. Better data sharing: Blockchain can facilitate the sharing of clinical trial data among different stakeholders, such as researchers and regulators, in a secure and standardized way, which can help to accelerate the discovery of new treatments and therapies.

d. Patient empowerment: Blockchain can enable patients to control their own health data and decide who can access it, which can help to improve patient engagement and trust in the clinical trial process.

For this invention, various data elements in an EMR can be used for creating NFT collections or blockchain based records. Some of the data can include:

Patient demographics: Name, date of birth, sex, address, phone number, email, and emergency contact information.

Medical history: Past and present medical conditions, allergies, immunizations, surgeries, hospitalizations, and family medical history.

Medications: Current and past medications, including prescription medications, over-the-counter medications, and herbal supplements.

Vital signs: Measurements of blood pressure, heart rate, respiratory rate, temperature, height, and weight.

Laboratory and diagnostic tests: Results of blood tests, urine tests, imaging studies, such as X-rays, CT scans, and MRIs, and other diagnostic tests.

Progress notes: Documentation of clinical encounters, including patient symptoms, diagnoses, treatments, and follow-up plans.

Immunizations: Record of immunizations administered to the patient, including the type of vaccine, date of administration, and location of administration.

Procedures: Documentation of medical procedures performed on the patient, including the type of procedure, date, and any associated complications.

Referrals: Documentation of referrals to specialists or other healthcare providers.

Advance directives: Documentation of patient preferences for end-of-life care, such as living wills or Do Not Resuscitate (DNR) orders.

Health maintenance: Documentation of preventive care measures, such as cancer screenings, mammograms, and flu shots.

Patient education: Documentation of patient education provided by healthcare providers, including patient handouts and educational materials.

Care team information: Information on the patient's care team, including healthcare providers and their contact information.

Insurance information: Including information about the patient's health insurance coverage, such as the name of the insurance company, the policy number, and the group number, co-pay amount, deductible, pre-authorization requirements, medication coverage, etc.

These EMR data fields can help healthcare providers understand a patient's history and plan for their healthcare needs. Knowing these requirements in advance can help healthcare providers avoid delays in care and ensure that the patient receives the appropriate treatment. Transparency of information helps individual care teams understand the overall picture of a patient's health and coordinate for a better experience.

In addition to EMRs, clinical trials are a second parallel branch of medication that accrues a lot of critical patient data and yet suffers from similar inefficiencies as pertains to transparency, ownership, and security of the data generated when conducting a clinical trial. Clinical trials are scientific studies designed to test the safety and effectiveness of new drugs, medical devices, treatments, or interventions in humans. Clinical trials are conducted to determine whether a new treatment is safe, effective, and has potential benefits that outweigh its risks. Clinical trials are typically conducted in phases, with each phase designed to answer different questions about the safety and efficacy of the treatment being tested. The following are the phases of a typical clinical trial:

Phase 1: This phase involves a small group of healthy volunteers who are given the treatment to determine its safety and dosage.

Phase 2: This phase involves a larger group of patients who have the disease or condition that the treatment is designed to address. The goal of this phase is to determine whether the treatment is effective and to gather more information about its safety.

Phase 3: This phase involves an even larger group of patients and is designed to confirm the efficacy and safety of the treatment in a real-world setting.

Phase 4: This phase is conducted after the treatment has been approved by regulatory bodies, and is designed to gather additional information about the long-term safety and effectiveness of the treatment. Clinical trials are typically conducted in a controlled setting, and participants are carefully monitored during each phase and throughout the trial to ensure their safety. The results of clinical trials are used to determine whether a new treatment is safe and effective, and whether it should be approved for widespread use.

Each phase of the clinical trials has its own set of objectives and goals measured with very specific data and trial endpoints. Any errors that may creep into the data, whether intentional or unintentional may cause large scale impact on the trial itself. Since it may be hard to recruit patients for a given set of diseases or symptoms, it is not uncommon for trials to be conducted in various locations, sometimes around the world. As such, there is a high probability that data errors may creep in, if the processes are lax. Clinical trials can be managed by big pharmaceutical companies themselves, or they may be outsourced to Contract Research Organizations (CROs) who are responsible for the entire scope of such trials. CROS play a significant role in the conduct of clinical trials. CROs are companies that provide outsourced research services to the pharmaceutical, biotechnology, and medical device industries. The typical steps involved in conducting clinical trials are: a) Study design: Design and develop clinical trial protocols and study plans that meet regulatory requirements and scientific standards; b) Patient recruitment: Recruit eligible patients for clinical trials, including identifying and contacting potential participants, and providing logistical support for enrollment; c) Site selection: Identify and select appropriate clinical trial sites, including negotiating contracts with study sites, and coordinating the regulatory and ethics approval processes; d) Data management: Manage the collection, analysis, and reporting of clinical trial data, ensuring data quality and integrity; e) Monitoring: On-site or remote monitoring of study sites to ensure compliance with the study protocol, Good Clinical Practice (GCP) guidelines, and regulatory requirements; f) Safety reporting: Manage safety reporting and adverse event management, including tracking and reporting adverse events to regulatory authorities; and g) Project management including coordinating study timelines, budgets, and resources.

The role of blockchain technology and specifically using NFTs in clinical trials can help to reduce the workload and cost for sponsors, while ensuring that clinical trials are conducted in a compliant and ethical manner, documenting the provenance and ownership of data at each stage as a trial progresses. For example, NFTs can be issued to patients as an identifier and an NFT collection can represent a cohort of patients with similar symptoms, responses, dosage, or any other parameter that is being tracked for the patient. A patient enrolled in a clinical trial can have multiple NFTs associated with them, depending on the data they are being monitored for. NFTs can also be issued for each provider based on various clinical trials that they have been a part of. This could then be an aggregated data set for the various capabilities and resources that the particular provider or facility can bring to the ecosystem, thereby establishing a transparent way of comparing various providers. NFT records and collections can also be created for various regulatory processes, specified as metadata or otherwise associated with the NFT and each patient record could be classified with those collections. Other data that can be associated with clinical trials represented as NFTs may include but not limited to demographic data, medical history of patient, vital signs before, during and after a test, lab test reports, adverse events, efficacy endpoints, quality of life measured along various parameters, compliance and protocol information, list of concomitant medications, safety data, data on drug metabolism, data on drug mechanism of action, imaging data, genetic data or other biomarker data that may be of interest. Other data as detailed above with EMRs may also be of specific interest when creating a blockchain and NFT based system for health records.

The invention provides a powerful framework for representing and managing health records on the blockchain for example health records associated with clinical trials. Regular patient health records not implicated in clinical trials are also anticipated by the invention. The health records represented as NFTs can carry immutable metadata detailing their origin, patient history, symptoms, treatments, drug interventions, imaging and so on.

Immutable refers to the inability to modify or tamper with data once it has been recorded. Transactions and data recorded on a blockchain are immutable, which means that they cannot be altered or deleted retroactively. This immutability is achieved through cryptographic hashing and the decentralized consensus mechanisms employed by blockchain networks. The immutable nature of blockchains ensures data integrity, transparency, and an auditable trail of all activities, which is crucial for applications requiring tamper-resistant record-keeping and trustless interactions. Data can also be stored immutably over the InterPlanetary File System (IPFS), which uses content-addressing to store immutable data in a distributed file system. This complements the immutable data storage capabilities of blockchains. Data can be stored on IPFS instead of directly on a blockchain due to the significant storage constraints and costs associated with recording large amounts of data on most blockchain networks. By storing the data immutably on IPFS and recording just the content-addressed IPFS hash on the blockchain, applications can leverage the immutability and tamper-resistance of both systems while optimizing for efficient data storage.

Ingesting data is the process of importing assorted data files from one or more sources into a cloud-based or on-premise storage medium, a data warehouse, data mart, InterPlanetary File System (IPFS), decentralized storage network, or any other structured or unstructured database where it can be accessed and analyzed. This process involves extracting data from various sources, transforming it into a compatible format, and loading it into the designated storage or a processing system. Efficient data ingestion mechanisms are crucial for handling large volumes of data from multiple sources in real-time or batch modes. The ingested data can encompass various formats, including text, numerical data, audio, video, and multimedia content. The ingested data can originate from databases, log files, IoT devices, social media platforms, or any other data-generating source, enabling organizations to consolidate and derive insights from diverse data sets. Robust data ingestion pipelines ensure data integrity, scalability, and integration with downstream analytics and processing systems.

A backpack is a cryptographic construct that binds a user's digital identity, data, credentials, or any other digital assets to a non-fungible token (NFT) or other blockchain-based token. This account backpack NFT serves as a secure, portable representation of the user's identity, data, credentials, and other assets across different applications. By leveraging the immutability and trustless characteristics of blockchain technology, the account backpack provides users with self-sovereign control and management of their digital identity and assets within a unified repository while maintaining security, transparency, and an auditable record of account activity.

Binding refers to the cryptographic process of associating a user's digital identity, credentials, assets, or data with a specific blockchain token or non-fungible token (NFT). This binding establishes an inseparable link between the token and the account, ensuring that the account's contents are inextricably tied to the token's ownership and transfer. The binding mechanism leverages cryptographic primitives like digital signatures and hashing to create a secure and verifiable connection between the account data and the fungible or non-fungible tokens. Once bound, the account and its associated data can only be accessed, modified, or transferred by the rightful owner of the corresponding token, as established by the private key/wallet address pair, providing self-sovereign control over the digital assets, identity and credentials.

A series of NFTs may refer to a chronological sequence of recorded activities, actions, or occurrences. Each NFT that is created in the series may be appended as an immutable entry, preserving the order and integrity of the overall series. The series of NFTs therefore allows for a transparent and auditable log of all events that have transpired within a system or process. As such, the system ensures a verifiable history that cannot be retroactively modified, enabling trustworthy record-keeping and traceability of operational activities over time.

An interval represents a specific, finite period or window of time that is consumed or utilized in its entirety. An interval has a defined start and end point. Once an interval has been allocated or assigned for a particular purpose, it cannot be reused or reassigned until it has been fully consumed or expired. This property of intervals ensures exclusivity and prevents overlapping usage conflicts within the designated time window. For example, if data from a particular interval has been converted to an NFT for audit purposes, the same data may not be included in another interval for a second NFT, as it may lead to double counting of the resources utilized in the interval. Such double counting can lead to conflicts and destroy the integrity of the data.

Health records that are minted as NFTs can be bound to the same wallet address or the same smart contract representing a collection of health records from a particular clinical trial, a provider, or any other health care entity such as a clinical research organization. Additionally, each clinical trial, provider, or healthcare entity itself can be represented as an NFT with its corresponding metadata. The clinical trial, provider or healthcare entity NFT can also be a backpack token. This allows for associating any future patient health records related to the clinical trial, provider, or healthcare entity to be associated with them by binding it to the backpack token. The Logicware platform allows healthcare entities, issuers, and holders to leverage advanced smart contract functionality for automated issuance, and consumption of such tokens and create their own set of actions based on the data bound to these tokens. smart contracts may also be bound to NFTs to create smart wallets.

Smart contracts can also enforce rules around patients, patient data, clinical trials, locations, provider capabilities, healthcare entity types, and geographic regions to ensure transparency and compliance. For example, clinical trial data from a specific clinical trial for a research project can be collected. The data can be broken into its desired parameters and minted as NFTs for example based on gender, age, demographic information, pre-existing conditions, or grouped based on placebo or monitored for the outcome of the treatment administered in the clinical trial. These can be created as separate NFTs with their own metadata and labels. Further, data from all events of the clinical trial can be grouped and represented as a comprehensive clinical trial dataset with its own NFT, metadata and labels. This can also be achieved by grouping the various NFTs corresponding to individual patient records minted as NFTs, for example by using ERC998, ERC6551, ERC4337, or any other relevant standards for composable NFTs (or an equivalent standard on a non-EVM blockchain).

Any health records that are minted as NFTs can be bound to a smart wallet address or the same smart contract used for creating a collection of the health records. Logicware also enables the bundling of health records into diversified portfolios based on preferences like gender, age, demographic information, pre-existing conditions, or grouped based on placebo or monitored for the outcome of the treatment administered in the clinical trial. For a clinical trial the NFT minting may be attested to by the provider or another healthcare entity. Attestation can additionally be recorded immutably on a blockchain.

Patient health records or clinical trial data can be attested. Such attestation can be optionally recorded on a blockchain. Such attestation enables users to verify and attest to real-world information and data on the blockchain. It allows for the creation of secure, privacy-preserving attestations that can be used for various purposes, such as identity verification, credential issuance, and data authentication. By leveraging attestations on a blockchain, organizations and individuals can establish trust and transparency in the verification process, as the attestations are recorded in an immutable and tamper-proof manner. This can have significant implications for sectors like finance, healthcare, and education, where reliable attestations of identities, credentials, and data are crucial.

These attestations can simply be implemented using the Logicware platform that provides a combination of smart contracts, and off-chain data storage:

Off-Chain Data Storage: The actual sensitive datasets or documents that need to be attested (e.g., AI models or training datasets, weights, identity documents, credentials, or records etc.) are stored off-chain in a secure storage facility such as a cloud environment or a decentralized storage such as IPFS.

Hashing and Encryption: The off-chain data is hashed using cryptographic hash functions, and the resulting hash is encrypted using the public key of the attesting entity (e.g., an enterprise user who wants to submit the attestation).

Smart Contracts: A set of smart contracts deployed via the Logicware manage the attestation process. These contracts handle tasks such as registering and authorizing attesting entities, storing and verifying encrypted hashes of attested AI datasets or AI models, and issuing and revoking attestations. In addition, the Logicware platform provides APIs for attestation verification.

Attestation Issuance: When an entity wants to attest to a piece of data or document, they encrypt the hash of the datasets or the AI models using their private key and submit it to the smart contracts. The contracts record the attested hash on the blockchain, along with metadata about the attesting entity and the attestation type.

Attestation Verification: To verify an attestation, the interested party (e.g., a service provider or another entity) can use the Logicware APIs to query the smart contracts, providing the encrypted hash and attestation metadata. The smart contracts can then confirm if the attestation exists and is valid, without revealing the actual underlying data, AI datasets or AI models.

Data Retrieval: If the attestation is valid, the interested party can retrieve the encrypted hash from the blockchain and use the attesting entity's public key to decrypt it. They can then compare this hash against the hash of the AI datasets or AI models they have, confirming its authenticity and integrity.

By leveraging smart contracts, cryptographic hashing, and off-chain data storage, Logicware platform enables secure and privacy-preserving attestations on the blockchain.

The Logicware platform supports various advanced authentication schemes like biometrics or multi-factor access controls. This enhances security and privacy for health records and accounts managed by corporations, governments, or healthcare entities. The immutable and transparent nature of the blockchain provides an auditable ledger for tracking the provenance and transaction history of each health record minted as a token. This traceability minimizes fraud, and inefficiencies in administering of health care and also any process inefficiencies as part of clinical trials.

There are additional advantages of representing health records as NFTs. Such representations for health records provides a clear lineage of medical history and interventions information. It may also be recognized by those skilled in the art that the present invention can work in addition to other monitoring and control systems, ingesting information from such systems and making it transparent for governance, reporting and audit purposes. In case of multiple healthcare organizations involved in administering patient care, the health record reporting may be represented as separate NFTs and combined together. The entire chain of records from multiple organizations may be represented as a single NFT, or as a set of nested NFTs, where all the NFTs may be grouped and/or owned and/or bound by the same wallet or a smart wallet.

The rest of the description below applies irrespective of whether the data is recorded in an EMR or if it is recorded for clinical trial purposes.

The platform described in the invention takes the complexity of the blockchain environment and abstracts it into a set of APIs and SDKs that can manage the entire process easily. For example, crypto wallets are front end technologies that require user interaction and input to mint an NFT from a smart contract. NFTB has turned it around and For clinical trials outcomes the primary endpoints are critically examined by regulatory bodies like the FDA when evaluating new drug applications or medical device approvals. The invention utilizes NFTs to enhance transparency of such data, storing it immutably and reporting the trial results to the regulators.

When a clinical study is complete, the cryptographic hashes representing the comprehensive outcome datasets can be recorded as NFTs on a blockchain. These NFTs can immutably store trial metadata such as the study protocol, sample statistics, data dictionaries, and analytic code used for statistical analysis. These NFTs can further be attested publicly by the healthcare entity conducting the trial, the doctors or physicians under whom the trial was being conducted or any other trusted third party. Regulatory reviewers can then independently validate the reported outcomes by replicating the analysis using the provenance data encoded in the NFTs. These NFTs can also be bound together in a smart wallet based on a variety of factors such as trial location, trial date, trial outcome, etc. Each of these bonded sets can be a part of a backpack token NFT that has the common traits of such NFTs as its metadata.

Such an approach provides an auditable chain-of-custody for outcome data, mitigating risks of data tampering or selective reporting. If an NFT is generated for every incident or patient encounter at the clinical trial level, the risk of selective or untimely reporting can be minimized. It enforces transparency by ensuring reviewers access the same data and methodologies as the trial sponsors. Confidential patient data need not be revealed to any unauthorized entities. This is accomplished by storing a hash of the patient data and making it publicly verifiable using digital signatures rather than storing encrypted or unencrypted data on the blockchain. To enhance security, zero knowledge proof protocols can be deployed. Such proofs assert that the analysis was executed correctly on authenticated data without revealing the underlying patient data.

Additional smart contracts can be deployed on the Logicware platform to automate disclosure rules, only revealing confidential patient data to authorized regulators while preserving privacy.

Furthermore, these outcome-representing NFTs create a permanent record on the blockchain, retrospectively enabling investigation of potential misconduct or re-analysis using new statistical techniques. This system provides a novel way of reporting clinical data, outcomes, protocols, and any other information to regulatory bodies like the FDA with comprehensive data.

Backend and middleware technology moves the complexity away from the user and providing for interaction via APIs and SDKs. As such any front end application can now interact with the blockchain without burdening the users with the intricacies of storing or managing their private keys and authorizing transactions to sign transactions to interact with the blockchains and mint, redeem, or create NFTs. A proxy process can be deployed in the backend that abstracts the user signatures as part of the transaction. At the backend, the transactions can also be handled by custodial wallets, or multi-signature wallets that can associate the transactions to the user accounts. The backend is capable of supporting multiple applications simultaneously and while each application may be deployed by a unique customer. The NFT engine 110 maps the backend databases, digital assets, and the blockchain layer interaction to provide a simple workflow for businesses and enterprises.

The middleware LogicWare also provides for creating wallets with various ways of protecting the private keys. A private key is a highly confidential key that authorizes transactions on the blockchain, proving ownership of the associated digital assets. The wallet address is the public counterpart, similar to a public address, that serves as a store of digital assets. The private keys can be stored on a Hardware Security Module (HSM), or in Key Management Systems (KMS), whose keys may be further entrusted to an encrypted vault. The keys can also be managed using a multi party computation (MPC) process that enables multiple parties to jointly compute a function without revealing their private inputs to each other. As part of the key management contemplated by this invention, LogicWare can distribute the private key across multiple parties in a way that ensures that no single party has access to the full private key. Instead, each party holds a share of the private key, and only by combining all shares can the full private key be reconstructed. Finally, irrespective of the key security mechanism described above, if at any time, a holder of the private key so desires, they can take complete control of their private keys via LogicWare.

For users of such a system, it is important that the system should be easy to use and also provide for secure authentication. From a compliance perspective it is also important that the system not allow for deconstruction of personal identities based on health records. As such, authentication plays an important role. An authentication module can optionally store login information and authenticate users against the blockchain information. As detailed below, the system can deploy decentralized IDs to enable selective disclosure of information or identity attributes. A user's public key may be stored on the blockchain which allows anyone to verify the authenticity of messages, transactions, or other data associated with that identity. A user in the ecosystem (patient, provider, insurance provider, etc.) may store identity-related data on the blockchain, such as verifiable claims, which are claims that have been cryptographically signed by a them and can be verified by others without revealing any additional information about the identity. Also, Zero knowledge proofs can be implemented to ensure that information about a user can be verified without sharing any personally identifiable information or protected information. Finally, verified credentials can also be deployed to ensure trustworthiness of the system.

A verified credential as part of this disclosure is a digital representation of a piece of identity-related data that has been cryptographically signed by a trusted authority. These credentials can include things like a person's name, date of birth, address, or medical record number or any other information as defined above relevant to EMR or clinical trials data. In a DID system, verified credentials are used to help establish trust between different parties. For example, when a user wants to prove their identity to a service provider (hospital, pharmacy, laboratory etc.), they can present a verified credential that has been issued by a trusted authority such as insurance company, a government agency or any other trusted participant in the ecosystem. The service provider can then cryptographically verify the authenticity of the credential without having to rely on a centralized identity provider. These verified credentials can be stored on the blockchain, along with the decentralized identity and associated public keys. This allows them to be accessed and verified by anyone in the network without the need for a centralized intermediary. Additionally, because the credentials are cryptographically signed, they cannot be tampered with or altered without detection. Overall, verified credentials help to provide a more secure, private, and flexible approach to identity management, enabling individuals and organizations to assert and control their identities without relying on centralized intermediaries.

The NFT engine 110 offers a range of features tailored for the healthcare ecosystem. Users can include patients, providers, administrators, pharmacies, insurance providers, clinical research organizations (CROs), nursing facilities, hospice care providers, and other participants. Location information is available from various sources managing patient data, allowing providers to map physical locations to health records, thereby establishing the authenticity and provenance of the data.

Optionally, geofences can be configured around hospitals, labs, provider facilities, and other physical locations to enhance data security or restrict interactions to those within the geofenced area. When a user enters a geofenced area, they can interact with the application. The LogicWare platform, along with APIs and SDKs, allows electronic medical records (EMR) or clinical trials applications to be developed as single web apps, native mobile apps, monolithic client applications, or distributed across client and server ends with separate roles for users and admins.

Entities with patient records can add location information to EMR or clinical trial records or create patient records directly on the blockchain when entering a geofenced area. The application can be triggered by scanning a QR code, using a specific URL, automatic backend configuration, or receiving a work order via SMS or message for diagnosis, lab tests, insurance claims, etc. The application can support single sign-on (SSO) or SAML assertion within an application. Users can log in using email, social networks, SSO, or SAML assertions and associate their login details with a blockchain wallet address, storing the corresponding private key. The application can also create a decentralized identity wallet for users, with verified credentials mapped to their profile information, ensuring the identity's authenticity without revealing personal details.

Users can claim their medical records as digital assets by presenting their public/private key pair to an application configured with a smart contract. These records or assets can be redeemed or claimed via fiat payment, cryptocurrency, redeem codes, or through whitelisted wallet addresses. The system can also blacklist wallet addresses to block interaction. Private keys are optional for redeeming assets, as the system can create records using system private keys or multi-sig techniques.

The application is governed by smart contracts, which can be EVM-compatible or custom-developed for specific blockchains like Near or Solana, and can run on public blockchains like Solana, Near, Aptos, or private blockchains like Hyperledger. Smart contracts support unique digital assets (ERC 721), copies of assets (ERC 1155), mixed digital assets (ERC 998), semi-fungible tokens (ERC 3525), and short-term access (rental) of medical records. Assets created via smart contracts can be imported into metaverse or 3D environments, overlaying medical records and images over 3D body scans, all mediated by ownership rules.

The Logicware application allows for on-the-fly smart contract deployment, creating a separate private key/wallet address pair for deployment. This deployment wallet may hold cryptocurrencies and pay for transactions related to the digital assets, or the cost may be borne by the buyer. The solution can be part of an enterprise deployment, with smart contracts configured and deployed via API calls in real-time, across various blockchains or test environments.

Digital assets are created and stored, with creative elements like pictures, audio, or video content, and associated data stored as metadata. This data can be stored centrally on internet-connected servers or in a decentralized manner using protocols like IPFS or Arweave. Digital assets may or may not be transferable to other wallet addresses on the blockchain. Payment confirmations, including token IDs, are stored on the blockchain as proof of payment when tokens are minted. In some embodiments, NFTs can be issued within one geofenced location and redeemed in another, with additional rules or requirements layered on top of geofencing rules.

The NFT engine 110, in an embodiment, mints and allocates cryptographic experiential tokens based on a location-based event and entitling the user to access an experience. In another aspect, token-gated access is granted to a resource at a location based on location triggered events and providing access to token-gated content in response to a user satisfying specified token criteria.

The system 100 may employ computer code modules (e.g., smart contracts) configured to manage the assignment of the non-fungible cryptographic tokens to designated digital wallet addresses associated with corresponding owners of the non-fungible cryptographic tokens. Digital wallets, or e-wallets or cryptocurrency wallets, can be in the form of physical devices such as smart phones or other electronic devices executing an application or electronic services, online services, or software platforms. Devices serving as digital wallets may include location-based services capabilities, e.g., GPS, UWB, BLE and other capabilities. Digital wallets may provide a store of value or a credit or access to credit and may be in the form of a digital currency or involve a conversion to digital currency, tradeable digital asset, or other medium of exchange. The stored value accessible using a digital wallet may involve authentication to access ownership records or other indica stored in a digital ledger or DLT and requiring authentication and/or other decryption techniques to access the store of value. Parties may use digital wallets in conducting electronic financial transactions including exchanges of digital currency for goods and/or services or other considerations or items of value. Transactions may involve use of merchant or other terminal equipment and involve near field communication (NFC) features or other communication techniques and use a computer network. In addition, digital wallets may include identifying or authenticating information such as account credentials, loyalty card/account data, and driver's license information, and the transaction may involve communicating information contained or stored in the digital wallet necessary to complete intended transactions.

The NFT health record module 120 can register and track health activity for individual consumers on a block chain. A patient health module 610 manages health information about an individual patient. A hospital module 620 interacts with public and private systems to aggregate health data for patients. An NFT processing module 630 uses a back end block chain system such as NFT engine 110 for NFT and blockchain transactions, preferably transparent to users. A network module 640 uses communication channels such as Ethernet and cellular data to exchange information across the data communication network 199.

In the context of healthcare records, NFTs could potentially be used to store and manage a person's medical records in a secure and decentralized way. This would allow individuals to easily access and share their medical information with healthcare providers, while also providing added security and protection against data breaches. In this system since the patients own and control their identity, decentralized identity and/or their own records, they are safeguarded explicitly by the user's private keys. Even if a central cloud system is hacked or otherwise compromised, the individual patient's records will still be safe as they would need to be unlocked with the patient's private keys.

APIs, or application programming interfaces, are a way for different software systems to communicate and share data with each other. In the context of using NFTs to manage healthcare records, an API could be used to allow different healthcare systems and providers to access and interact with a person's medical records in a secure and controlled way. For example, a hospital's electronic health record system could use an API to retrieve a person's medical history from the NFT-based system, or to update the records with new information. This would allow for seamless and secure sharing of medical information between different healthcare systems, while also maintaining the unique and tamper-proof properties of the NFTs.

Smart contracts are self-executing contracts with the terms of the agreement between two parties being written into lines of code. In the context of using NFTs to manage healthcare records, smart contracts could be used to automate certain processes and ensure that the records are always up to date and accurate. For example, a smart contract could be set up to automatically retrieve and update a person's medical records from multiple healthcare providers, or to ensure that the records are only shared with authorized parties. This could help to streamline the process of managing and accessing medical records, and reduce the potential for errors or inconsistencies. Additionally, because smart contracts are based on blockchain technology, they can provide added security and immutability to the NFT-based healthcare records system.

EMR, or electronic medical records, are digital versions of a person's medical history, including their medical conditions, treatments, and test results. EMR systems are often used by healthcare providers to manage and access a person's medical records.

Implementing NFTs and smart contracts into an EMR system could potentially bring several benefits. First, it could make it easier for healthcare providers to access and share a person's medical records, as the records would be stored in a decentralized and secure way. This could improve the efficiency of the healthcare system and help to ensure that patients receive the best possible care.

Second, using NFTs and smart contracts could help to protect against data breaches and unauthorized access to a person's medical records. Because the records would be stored on a blockchain and controlled by smart contracts, they would be highly secure and difficult to tamper with. This could provide added peace of mind for patients and healthcare providers alike.

Finally, implementing NFTs and smart contracts into an EMR system could also help to reduce the potential for errors and inconsistencies in a person's medical records. By automating certain processes and ensuring that the records are always up to date, the system could help to improve the accuracy and reliability of the information. This could ultimately lead to better healthcare outcomes for patients.

It should be noted that while the above describes a variety of use cases related to NFTs, the tips and techniques described in any one can be mixed and matched with others. For example, an NFT custodian for an insurance company can choose to encrypt custodial crypto wallet private keys with biometrics. Alternatively, they could choose to issue ERC998 standard tokens instead of ERC721. The permutations and combinations associated with the above are limitless and new use cases can easily be derived via a combination of some of the elements described above.

Figure 2:
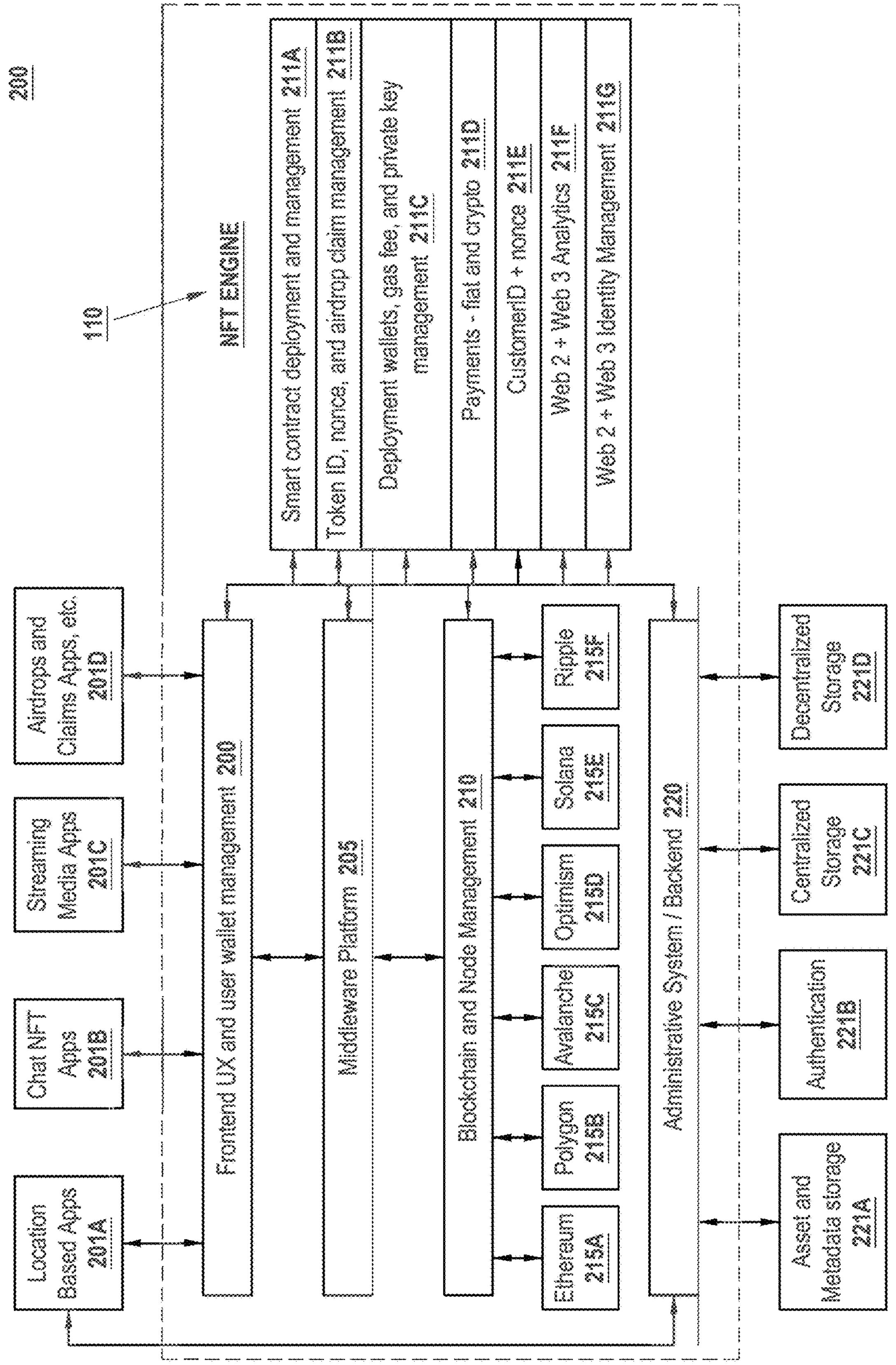
FIG. 2 is a more detailed block diagram illustrating an NFT engine of the system of FIG. 1, according to an embodiment.

FIG. 2 illustrates one embodiment of a high-level architecture of the NFT Engine and its components. Various other components and modules can be added to the NFT Engine to accommodate customized NFT requirements.

The NFT Engine 110 interfaces with a variety of other software modules including the user experience modules and the core software infrastructure modules. In one embodiment, 201A is a location based application that is built using the NFT Engine 110. Location based apps 201A could also be a non location based application or any other generic application that provides blockchain and NFT functionality to the users. NFT health record apps 201B is another application or module. Other applications from a user experience perspective may be streaming media or digital avatar apps such as 201C or AirDrop and claims applications such as 201D there may be many more applications that can be built on top of the NFT engine. These applications interface directly with the NFT engine via the front end UX and user wallet management modules 200. In addition these applications also interface with an administrative system or a backend, 220, which may be specific or customized for each application. The front end UX and user wallet management module 200 is connected to the NFT brewery middleware platform, 205, which in turn connects to blockchain and node management modules 210. It may be noted that all the components of the NFT engine may also be directly interconnected with each other to ensure proper data flow, data and identity management and access controls for the users. The administrative system or backend 220 connects to various blockchains including but not limited to Ethereum 215A, Polygon 215B, Avalanche 215C, Optimism 215D, Solana 215E, Ripple 215F, or any other EVM or non-EVM blockchain via custom RPCs and APIs. In addition the back end 220 provide support for asset and metadata storage 221A, authentication 221B, centralized storage 221C, or decentralized storage 221D. Other modules and components of the NFTEngine include:

1. Smart contract deployment and management module (211A), that supports any underlying blockchain
2. TokenID, nonce, airdrop claim management modules (211B) to ensure individual transactions can be processed out of sequence as well in case certain transactions are held up in the execution queue.
3. Deployment wallets and scripts, wallet management including private key management and gas management (211C), with a variety of ways for managing private keys including encryption, utilizing key vaults, multi party computation techniques (MPC) or multi-signature wallet management.
4. Payments modules for both fiat as well as cryptocurrencies (211D) via payment gateways, integrating recording the transaction results and status directly into the blockchain.
5. CustomerID and Nonce management for individual customers (211E), similar to user side described above, to ensure that transactions by different customers do not queue up and can be processed independently.
6. Integrated web2 and web3 analytics (211F) to map transactional information of users to their wallets. In addition, AI techniques and algorithms can be utilized to infer behavioral information about users independent of their demographic information.
7. Integrated web2 and web3 identity management (211G) that allows for access controls to be implemented based on the digital wallets, ownership of media or avatars, or any other digital goods or identity modules including SSO, SAML, etc.

Figure 3:
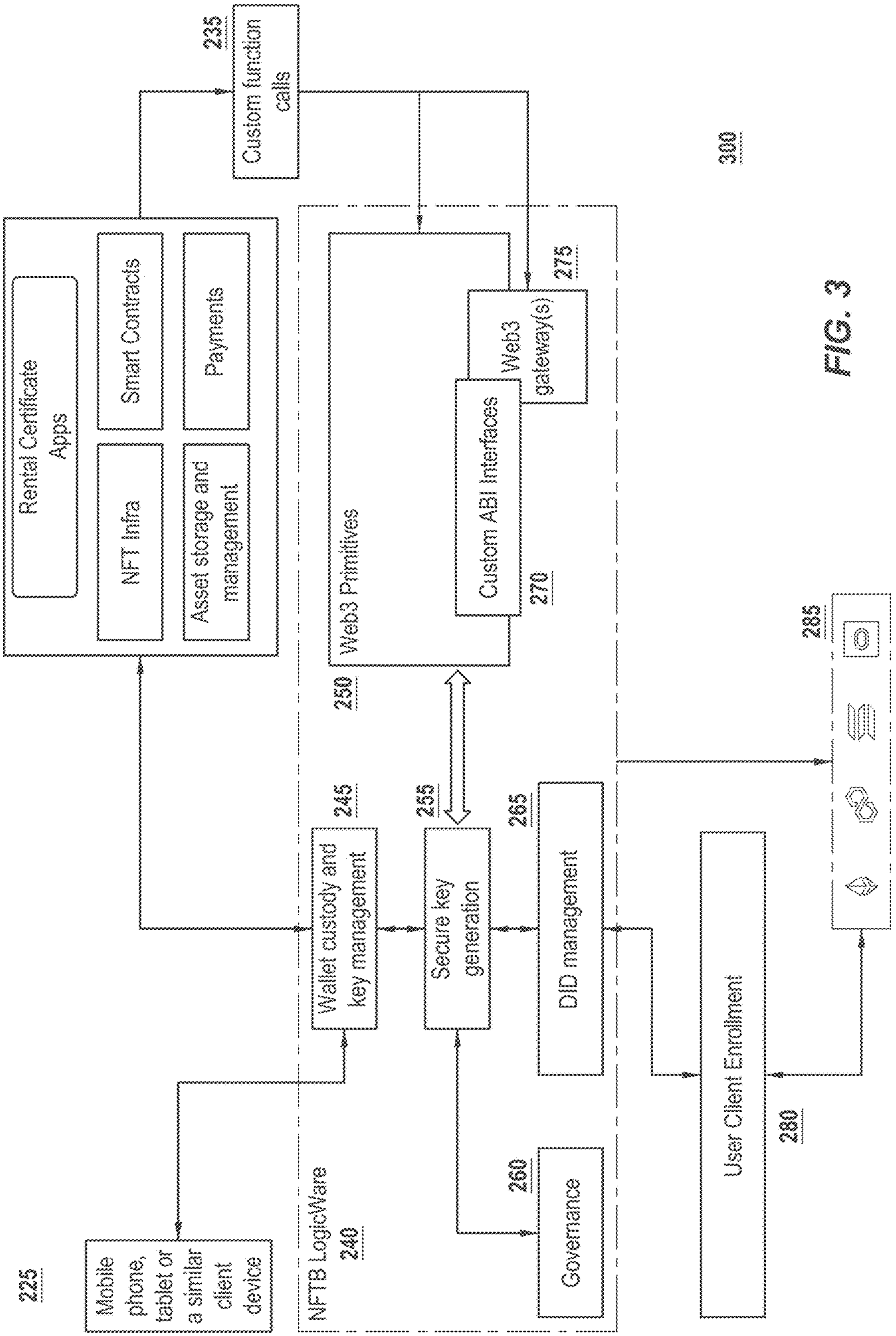
FIG. 3 is a diagram illustrating an EMR or a clinical trial business application, according to an embodiment.

FIG. 3 illustrates an exemplary high level architectural view of a sports NFT marketplace and applications using the current invention. The client in this case can be an athlete, a sports league, school, university, professional association, coaches, or any other entity or a service provider in the ecosystem. Various other components and modules can be added to this architecture to accommodate customized NFT requirements.

The end user may log in into the platform using a mobile phone tablet or similar client device 225. The application running on the device interacts with the NFT middleware platform via LogicWare 240. The LogicWare determines the wallet custody and key management protocol, 245, that applies to the particular application 230 or the user and logs the user in into the application. If the user interacts with the application or dApp the first time, the custody and key management protocol, 245, generates a new key pair using the secure key generation module, 255, or the user and associates it with their identity. Optionally it may also associate the keys with a decentralized identity and issue verified credentials to the user. Additionally, LogicWare also creates or associates the governance policies that the user identity may be subject to. If the user is a returning user, the LogicWare retrieves the keys and based on the governance and access control rights, allows the user to access the application or the dApp. As depicted in FIG. 2 the application or dApp may consist of several components including smart contracts deployed via the module 211A or otherwise imported into the application, NFT infrastructure modules such as 211A, 211B, 211C, 211D, 211E, 211F, 211G, etc., asset storage and management (221A, 221C, 221D), or payments 211D etc.

The application interfaces with the middleware and LogicWare 240, via custom function calls APIs and SDKs 235. The NFTB LogicWare includes various web3 primitives, 250, that are interoperable building blocks that are highly reliable in executing transactions over a blockchain, communicate with backend 220 and frontend 200 systems, work with storage components 221C, 221D, utilize analytics from modules such as web2 and web3 analytics 211F, identify users using the identity management module 211G, secure the applications using authentication, identity management, or implement access controls with 211G, 211B or provide for a governance layer in combination with the governance module 260. The web3 primitives 250, also communicate with custom ABI interfaces 270 and web3 gateways 275 for deploying smart contracts to their respective blockchains, interacting with smart contracts, and executing the functions and instructions in the smart contracts.

The LogicWare optionally comprises a governance 260 and a Decentralized Identity (DID) management module 265. DIDs are an important part of securing identity and making it interoperable across both web2 and web3 platforms.

Applications in web3 are also referred to as dApps. Governance in decentralized applications (dApps) in and communities refers to the processes and mechanisms through which decisions are made and actions are taken within the decentralized ecosystem. In traditional centralized systems, governance is typically controlled by a central authority, whereas in decentralized systems, governance is distributed among network participants. In one embodiment, the decision making and governance is in part based on the decentralized identity of the users themselves, who interact with the dApp and the associated smart contracts with their wallets and their corresponding private keys. The Governance module 260 within the NFTB LogicWare allows for implementing various governance mechanisms and resource allocations. In conjunction with the DID management module 265, the governance module 260 also employs mechanisms to prevent Sybil attacks or other malicious attacks on the system, such as, where an individual may create multiple identities to gain disproportionate influence for voting purposes. Sybil resistance mechanisms can include reputation systems, stake-weighted voting, or identity verification to ensure that governance decisions are made by genuine participants.

The DID management module 265 is a part of the web2 and web3 identity management module 211G described above. The module utilizes methods for decentralized technologies, such as distributed ledgers (e.g., blockchain) or peer-to-peer networks, to enable the creation, management, and verification of DIDs and associated digital identities. As such, the DID created for any user can be used as an identity across any blockchain and helps identify the user on the application, without compromising the user's actual identity or demographic information. The users retain full control over their DID and can choose to lock and selectively share their information using their DIDs. In particular, this is an efficient way of combining various private blockchain systems favored by enterprises, with the public blockchain systems. With a DID, a user can retain the same wallet address to make transactions over any supported blockchain.

Various blockchains may have different ways to monitor and govern the identity of the users. In order to map the identity from one system to another, it may be necessary to homogenize the identity across the multiple platforms by implementing a client enrollment module, 280, to create a system where the identities from one system may map directly to an identity on another system, without the need for any user intervention. For example, when making a private blockchain system to be compatible with a public blockchain such as Ethereum, Polygon or Solana, it may be essential to create a user (client) enrolment into the Hyperledger based system and map it to the private keys for the eventual user of the system.

Figure 5:
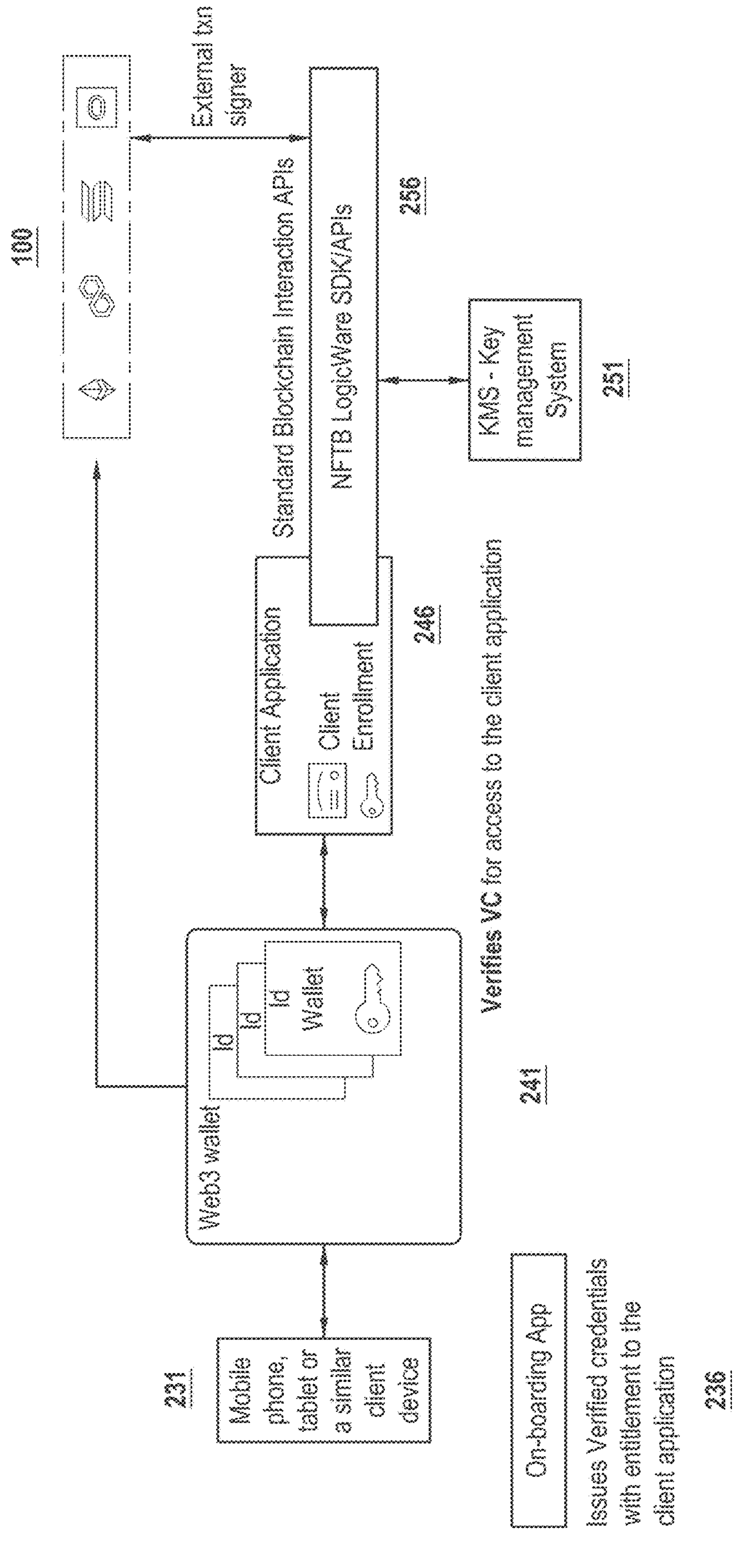
FIG. 5 illustrates the use of verified credentials (VCs) for authentication into the ecosystem of applications for access control or user onboarding features, according to an embodiment.
Figure 6:
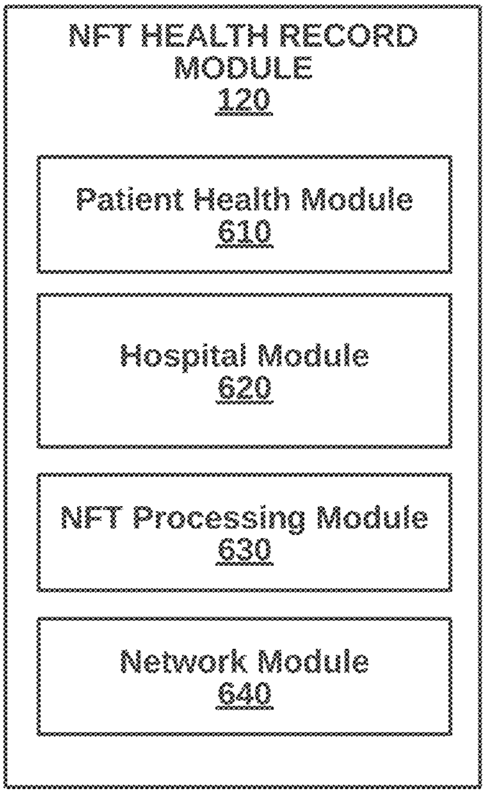
FIG. 6 is a more detailed block diagram illustrating an NFT health record module of the system of FIG. 1, according to an embodiment.

FIG. 5 illustrates the use of verified credentials (VCs) for authentication into the ecosystem of applications for access control or user onboarding features.

When a user logs in to the platform using a mobile phone, tablet, desktop, or a similar device, 231, the onboarding application, 236, or dApp issues a verified credential (VC), to the user. It may be noted that the VC may be issued by a third party application separately and imported into the client application. These VCs allow the user to access other connected applications or dApps that the user may wish to, such as loyalty programs, using their decentralized identity. As such verified credentials (VCs) act as authenticating mechanism for users to use the appropriate wallets as a proxy for their identity on the system. A user may have multiple wallets associated with their identity. When a user logs in to the application or dApp, the LogicWare, 256, identifies the appropriate identity to use and retrieves the appropriate keys from the key management system, 251. This in turn allows the application or dApp, 246, to transact with the blockchain using the appropriate identity and the private keys associated with them. A user's public key may be stored on the blockchain which allows anyone to verify the authenticity of messages, transactions, or other data associated with that identity.

A. Artificial Intelligence for Gathering and Analyzing Data

Figure 4:
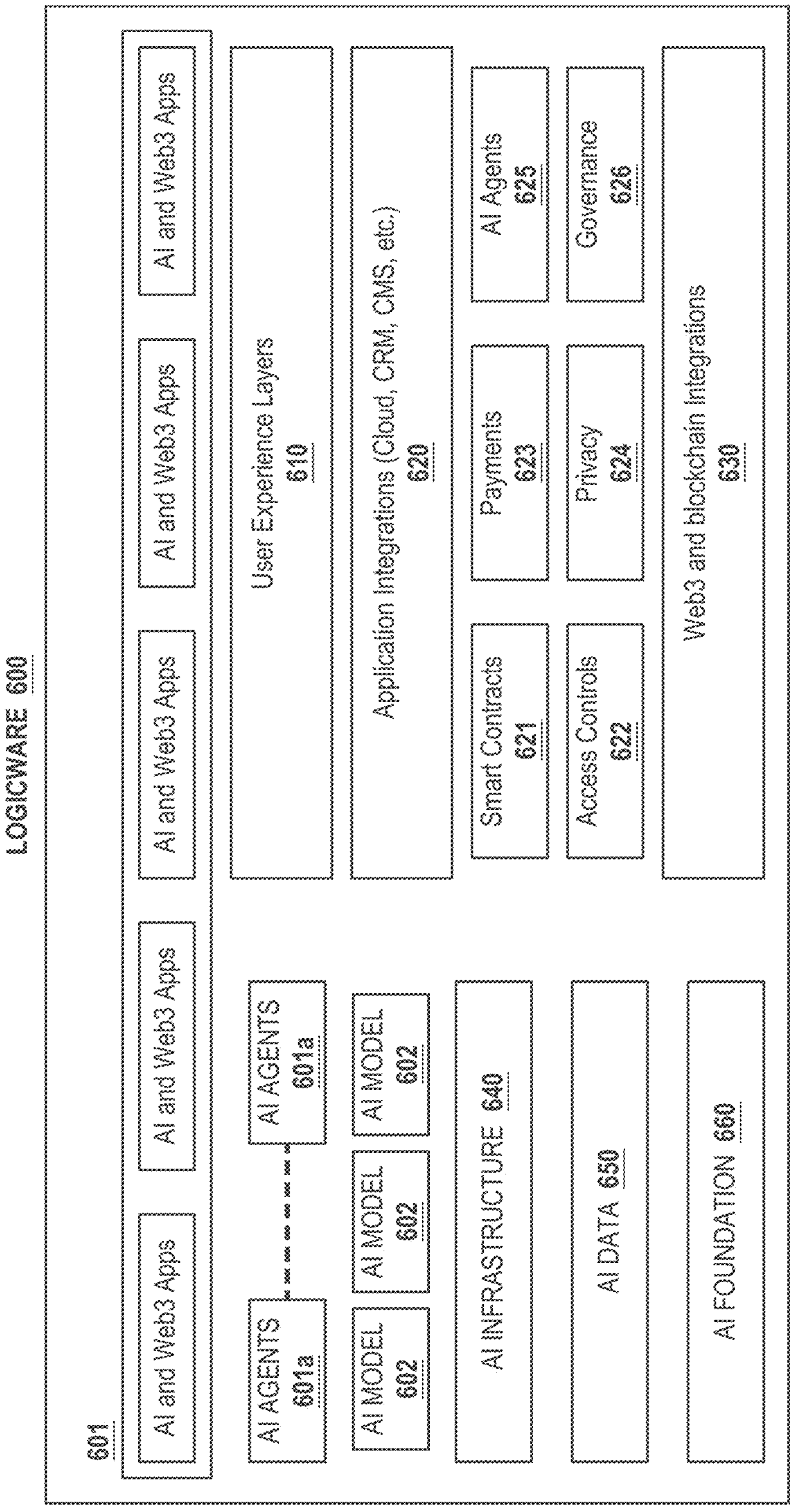
FIG. 4 is a block diagram illustrating the elements of the LogicWare with artificial intelligence, blockchain and Web3 interfaces, according to an embodiment.

FIG. 4 is a block diagram further illustrating elements of the LogicWare with blockchain, AI and Web3 interfaces.

The Logicware system 400 depicted in FIG. 4 abstracts away many of the complexities involved in building and operationalizing AI systems, enabling developers and applications to focus on leveraging AI capabilities rather than dealing with low-level infrastructure concerns. AI Foundation 660 refers to the underlying platform enabling the integration and deployment of artificial intelligence capabilities within LogicWare 600. The AI Foundation 660 serves as a common layer that provides essential services and components required for developing, deploying, and managing AI models and applications. AI Foundation may be part of the LogicWare 600 deployed as SDKs or made available to Logicware via APIs. AI Foundation may include or support the following key elements:

Data ingestion and preprocessing: Components for collecting, cleaning, and preprocessing data from various sources to prepare it for use in AI models. For example datasets for healthcare records can be used to train AI models and agents.

Model development and training: Tools and environments for building, training, and evaluating AI models 602, such as machine learning, deep learning, or natural language processing models.

Model management: Services for versioning, storing, and managing trained AI models 602, as well as monitoring their performance and updating them as needed.

Inference and deployment: Mechanisms for deploying trained AI models into production environments, allowing applications and systems to consume and leverage the AI capabilities.

Scalability and performance: Infrastructure 640 and services that enable the efficient scaling and high-performance execution of AI workloads, often involving specialized hardware like GPUs or TPUs and cloud-based services.

Security and governance: Mechanisms for ensuring the secure and compliant use of AI models, including access control, auditing, and adherence to regulatory requirements.

Integration and APIs: Interfaces with Application Integrations 630 and APIs that allow other applications and systems to seamlessly integrate and consume the AI capabilities provided by the foundation such as process systems 621-626.

AI Foundation 660 aims to provide a standardized and consistent platform for AI development and deployment with Logicware 110, across the organization, promoting reusability, scalability, and governance of AI solutions. Some of the features of the AI Foundation 660, may also integrate with cloud, CRM, CMS, clinical trials record management, CRO operations, and other systems via Application Integrations 620.

AI Data 650 refers to the information used to train and develop artificial intelligence systems. This data can be in various forms, such as text, images, audio, or numerical data, or any healthcare data, depending on the application of the AI system. Ensuring the quality, relevance, and diversity of AI data is crucial for building accurate and unbiased AI models. AI data can be both structured and unstructured:

1) Structured data refers to information that is organized and formatted in a predefined way, such as databases, spreadsheets, or labeled datasets. This type of data is typically used for tasks like classification, regression, or structured prediction problems.
2) Unstructured data, on the other hand, refers to information that does not have a predefined format or structure, such as text documents, images, audio files, or social media posts. This type of data requires more preprocessing and feature extraction techniques before it can be used for training AI models.
3) Many AI applications, especially in areas like natural language processing (NLP) and computer vision, rely heavily on unstructured data, while structured data is more commonly used in fields like finance, healthcare, and manufacturing.

Logicware works with both structured and unstructured data which can also be integrated via application integrations 620.

AI infrastructure 640 refers to the combination of hardware and software resources required to develop, train, and deploy artificial intelligence systems effectively. It includes powerful computing resources, such as GPUS, TPUs, or specialized AI accelerators, to handle the computationally intensive tasks involved in training large AI models. AI infrastructure also encompasses the software platforms, frameworks, and tools used for data preprocessing, model building, training, and inferencing, which may also be a part of the AI Foundation. Additionally, AI Infrastructure 640 may involve storage and data management solutions to handle the vast amounts of data required for AI model training. The system in FIG. 8 enables robust AI infrastructure is crucial for organizations to scale their AI initiatives and achieve efficient model development and deployment cycles.

AI models are mathematical representations or algorithms that are trained on data to learn patterns, make predictions, or take actions. They are the core components of artificial intelligence systems that enable them to perform specific tasks, such as image recognition, natural language processing, or decision-making. AI models can be deep learning models, like convolutional neural networks or transformers, or more traditional machine learning models like decision trees or support vector machines. The performance and accuracy of an AI model depend on the quality and quantity of the training data, the model architecture, and the techniques used for training and optimization.

AI agents are software programs that employ artificial intelligence techniques to operate autonomously or semi-autonomously in a variety of environments, making decisions based on input data, predefined rules, machine learning models, or a combination of these methodologies. Typically, AI agents are capable of performing tasks independently without human intervention, adjusting their actions based on the analysis of incoming data. In this way they are an extension of an analytics engine and make it easy to take actions based on the underlying analysis for the data that they operate upon, such as carbon credit information data. These agents can improve their performance over time through learning mechanisms, based on the data itself. They adapt by observing outcomes and integrating new knowledge into their decision-making processes, retraining their algorithms in light of the new data. AI agents continuously perceive their environment and can react to changes in real-time or near real-time. Beyond reactive behaviors, AI agents can also exhibit goal-oriented behaviors, initiating actions based on predictive analytics and strategic planning. The design allows these agents to handle increasing amounts of work or to be easily expanded to manage complex or additional tasks. The output of AI agents can be information that can be represented as metadata and associated with an NFT. In one embodiment AI agents can be used to process data and create metadata that can be immutably recorded and attached to an NFT.

These AI agents can be implemented using a variety of technical frameworks and methodologies, including but not limited to:

Machine Learning and Deep Learning: Utilizing algorithms and neural networks to analyze data, recognize patterns, and make decisions.

Natural Language Processing (NLP): Enabling the understanding and generation of human language, facilitating interactions between humans and machines.

Robotics: Applying AI in mechanical or virtual robots, connected devices, IoT (Internet of Things) devices, etc. allowing for physical interaction with environments.

Expert Systems: Incorporating rule-based systems that mimic the decision-making abilities of a human expert.

Data Analysis Systems: Designed to interpret vast datasets efficiently and accurately to derive meaningful insights.

In FIG. 4, system 400 can support a range of AI and Web3 applications via interfaces 601. AI applications can be utilized in a wide range of fields, including computer vision for object detection and recognition, natural language processing for text analysis and generation, predictive analytics for forecasting and decision support systems, as well as robotics and automation for task planning and control. The proposed invention leverages novel AI models and algorithms to achieve improved performance, efficiency, or functionality compared to existing approaches. These applications can find use in a variety of different industries and for numerous use cases such as healthcare diagnostics, financial fraud detection, recommendation systems, language processing, customer service, etc. The AI application can be implemented on various hardware platforms, such as cloud computing infrastructure, edge devices, or specialized AI accelerators, enabling scalable and cost-effective deployment.

Various cloud vendors provide platforms and services that support the development and deployment of AI agents. These cloud vendors are continuously adding support features, improved capability and services in support of their cloud offerings. Some of the major providers include Amazon Web Services (AWS) (Amazon Lex: A service for building conversational interfaces into any application using voice and text; Amazon Polly: A service that turns text into lifelike speech, allowing users to create applications that talk; Amazon Rekognition: A service for adding image and video analysis to applications; Amazon Comprehend: A natural language processing (NLP) service for understanding the content of text documents; Amazon SageMaker: A fully managed service that provides developers and data scientists with the ability to build, train, and deploy machine learning (ML) models); Microsoft Azure (Azure Bot Service: A service that enables you to build intelligent, enterprise-grade bots that help enrich the customer experience while reducing costs; Azure Cognitive Services: A set of APIs, SDKs, and services available to help developers build intelligent applications without having direct AI or data science skills; Azure Machine Learning: A cloud-based environment that a user can use to train, deploy, automate, and manage machine learning models0; Google Cloud Platform (GCP) (Google Dialogflow: A natural language understanding platform that makes it easy to design and integrate a conversational user interface into mobile app, web application, device, bot, interactive voice response system, and more; Google Cloud Speech-to-Text and Text-to-Speech: APIs for converting audio to text and vice versa; Google Cloud Vision API: Enables developers to understand the content of an image by encapsulating powerful machine learning models in an easy-to-use REST API; and Cloud Natural Language API: Provides natural language understanding technologies to developers).

These cloud vendors offer a wide range of AI and machine learning tools and services, enabling developers to create sophisticated AI agents, chatbots and virtual assistants.

III. Methods for NFT Health Records (FIGS. 7-8)

Figure 7:
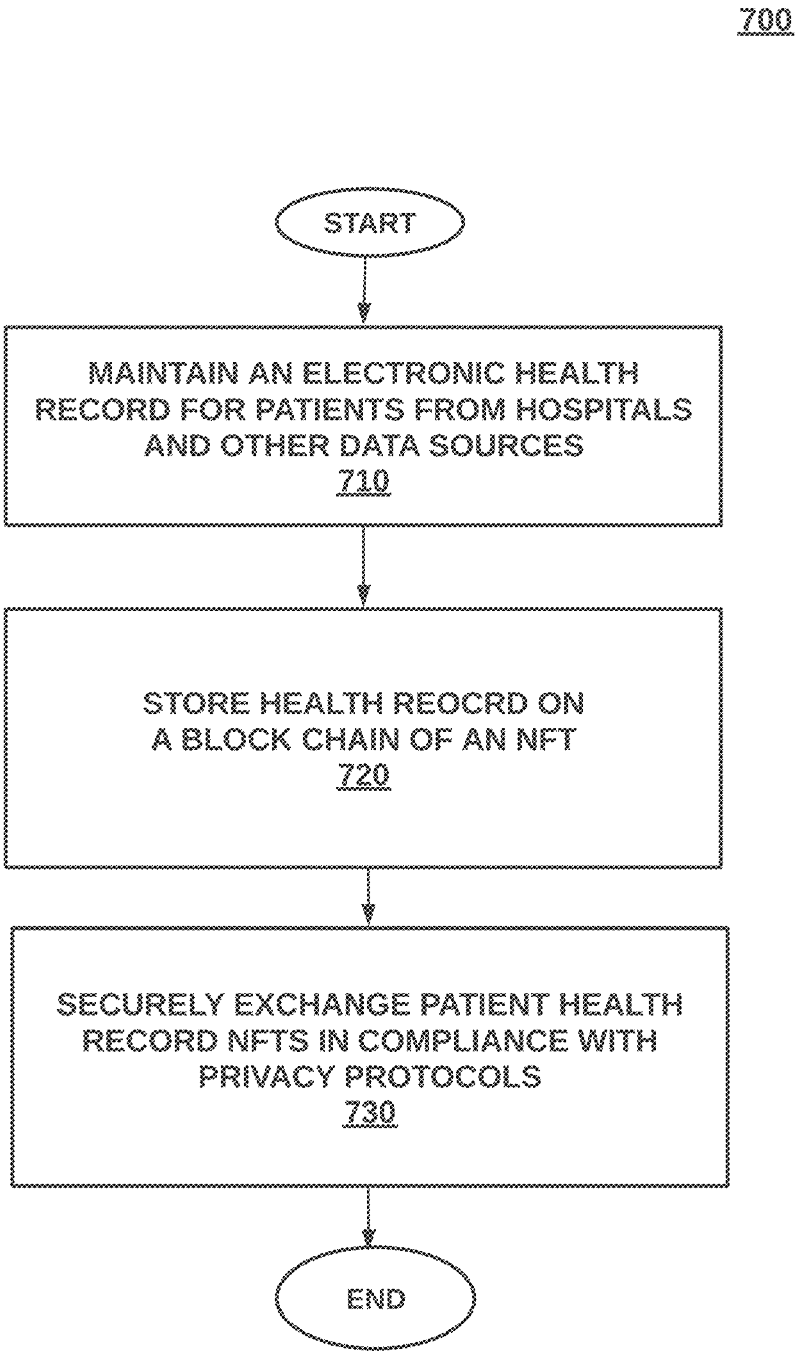
FIG. 7 is a high-level flow diagram illustrating a method for tracking and exchanging health records using NFTs, according to one embodiment.

FIG. 7 is a high-level flow diagram illustrating a method 700 for tracking and exchanging health records using NFTs, according to one embodiment. At step 710, health information about an individual patient is collected from public and private systems into an electronic patient record. At step 720, the data is stored on a block chain of NFTs and, at step 730, securely exchanged in compliance with privacy protocols.

Figure 8:
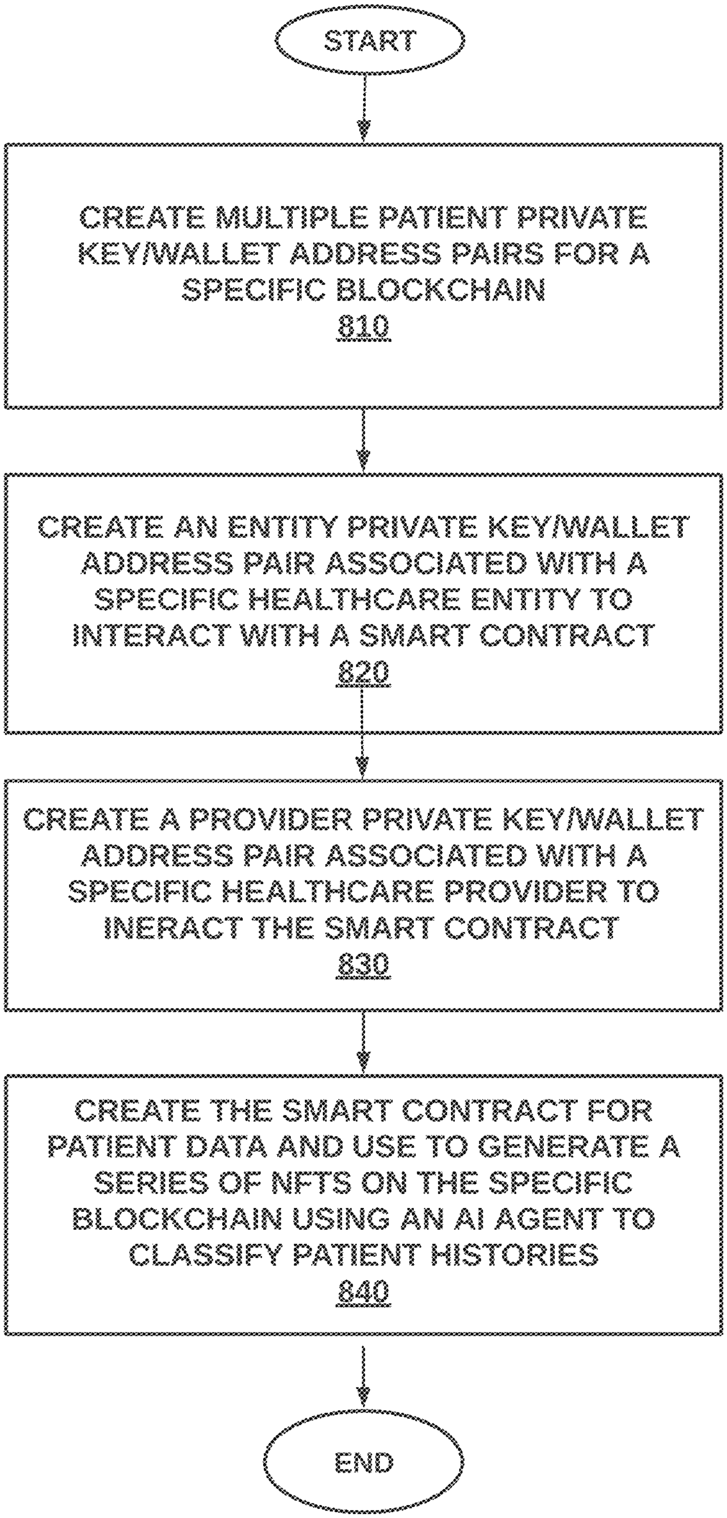
FIG. 8 is a more detailed flow diagram illustrating an alternative method for tracking and exchanging health records using NFTs, according to one embodiment.

FIG. 8 is a more details flow diagram illustrating an alternative method 800 for tracking and exchanging health records using NFTs, according to one embodiment.

At step 810, a plurality of patient private key/wallet address pairs is created. Each is associated with specific patient data to interact with the system to create a plurality of patient histories each associated with a patient, wherein the patient private key/wallet address pair is associated with a specific blockchain;

At step 820, an entity private key/wallet address pair associated with a specific healthcare entity is created to interact with a smart contract for the records for a clinical trial and store at least a portion of the patient data associated with the specific patient on the blockchain.

At step 830, a provider private key/wallet address pair associated with a specific healthcare provider is created to interact with the smart contract and store at least a portion of the patient data associated with the specific patient on the blockchain.

At step 840, the smart contract for patient data associated with a relationship between a specific patient and a specific healthcare entity or healthcare provider in a patient history database is created.

At step 850, a NFT in a series on the blockchain according to new patient data using the smart contract associated with the entity private key/wallet key pair of the patient data or the entity or the provider to activate the patient history is generated.

At step 860, using an AI agent to classify patient histories based on parameters identified in the clinical trial and create a cohort of specific patients based on matching the said parameters with metadata associated with the NFTs.

III. Computing Device for NFT Health Records (FIG. 9)

Figure 9:
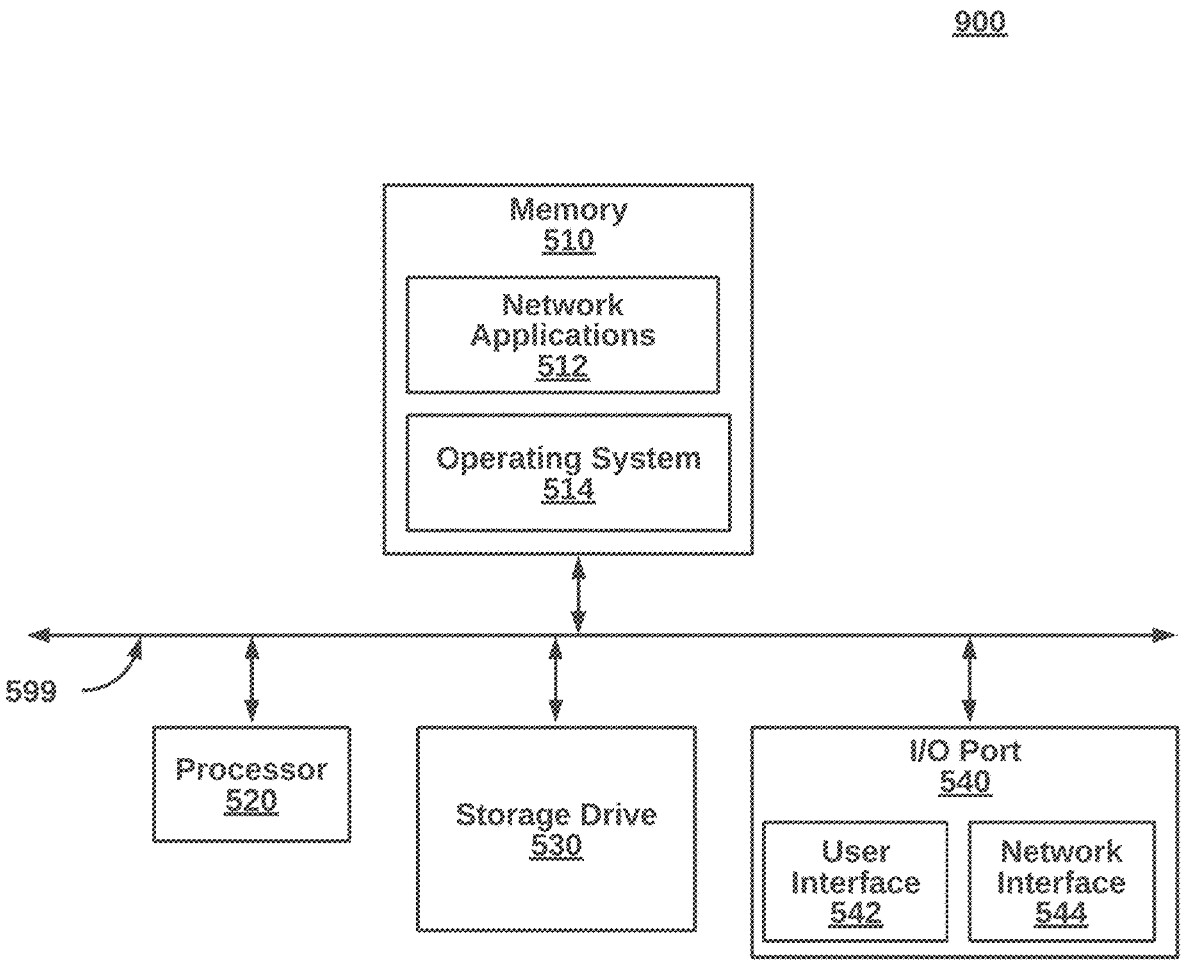
FIG. 9 is a block diagram illustrating an example computing device for the system of FIG. 1, according to one embodiment.

FIG. 9 is a block diagram illustrating a computing device 900 for use in the system 100 of FIG. 1, according to one embodiment. The computing device 900 is a non-limiting example device for implementing each of the components of the system 100, including NFT engine 110, NFT health record module 120, a patient device 130, and a hospital device. Additionally, the computing device 500 is merely an example implementation itself, since the system 100 can also be fully or partially implemented with laptop computers, tablet computers, smart cell phones, Internet access applications, and the like.

The computing device 900, of the present embodiment, includes a memory 510, a processor 520, a hard drive 530, and an I/O port 540. Each of the components is coupled for electronic communication via a bus 599. Communication can be digital and/or analog, and use any suitable protocol.

The memory 510 further comprises network access applications 512 and an operating system 514. Network access applications can include 512 a web browser, a mobile access application, an access application that uses networking, a remote access application executing locally, a network protocol access application, a network management access application, a network routing access applications, or the like.

The operating system 514 can be one of the Microsoft Windows® family of operating systems (e.g., Windows 98, 98, Me, Windows NT, Windows 2000, Windows XP, Windows XP x84 Edition, Windows Vista, Windows CE, Windows Mobile, Windows 7-11), Linux, HP-UX, UNIX, Sun OS, Solaris, Mac OS X, etc., Alpha OS, AIX, IRIX32, or IRIX84. Other operating systems may be used. Microsoft Windows is a trademark of Microsoft Corporation.

The processor 520 can be a network processor (e.g., optimized for IEEE 802.11), a general-purpose processor, an access application-specific integrated circuit (ASIC), a field programmable gate array (FPGA), a reduced instruction set controller (RISC) processor, an integrated circuit, or the like. Qualcomm Atheros, Broadcom Corporation, and Marvell Semiconductors manufacture processors that are optimized for IEEE 802.11 devices. The processor 520 can be single core, multiple core, or include more than one processing elements. The processor 520 can be disposed on silicon or any other suitable material. The processor 520 can receive and execute instructions and data stored in the memory 510 or the hard drive 530.

The storage device 530 can be any non-volatile type of storage such as a magnetic disc, EPROM, Flash, or the like. The storage device 530 stores code and data for access applications.

The I/O port 540 further comprises a user interface 542 and a network interface 544. The user interface 542 can output to a display device and receive input from, for example, a keyboard. The network interface 544 connects to a medium such as Ethernet or Wi-Fi for data input and output. In one embodiment, the network interface 544 includes IEEE 802.11 antennae.

Many of the functionalities described herein can be implemented with computer software, computer hardware, or a combination.

Computer software products (e.g., non-transitory computer products storing source code) may be written in any of various suitable programming languages, such as C, C++, C#, Oracle® Java, Javascript, PHP, Python, Perl, Ruby, AJAX, and Adobe® Flash®. The computer software product may be an independent access point with data input and data display modules. Alternatively, the computer software products may be classes that are instantiated as distributed objects. The computer software products may also be component software such as Java Beans (from Sun Microsystems) or Enterprise Java Beans (EJB from Sun Microsystems).

Furthermore, the computer that is running the previously mentioned computer software may be connected to a network and may interface to other computers using this network. The network may be on an intranet or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, and 802.ac, just to name a few examples). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical access applications. This description will enable others skilled in the art to best utilize and practice the invention in various embodiments and with various modifications as are suited to a particular use. The scope of the invention is defined by the following claims.

We claim:

1. A patient health record system, on a data communication network, for creating privacy-preserving patient cohorts from a blockchain for a clinical trial, the patient health record system comprising:

a processor;

a network interface communicatively coupled to the processor and to the data communication network; and a memory, communicatively coupled to the processor and storing source code executed by the processor, comprising:

a patient health module configured to manage health information about a plurality of patients, including a specific patient, by maintaining a patient NFT series associated with a patient private key/wallet address pair, wherein a patient private key/wallet address pair is associated with the blockchain;

a hospital module configured to aggregate health information for the plurality of patients, including the specific patient, and detect a health event in a series of health events associated with the specific patient;

a smart contract bound to the patient NFT series and configured to apply clinical-trial recordation rules to determine whether the health event is to be immutably recorded on a blockchain for a non-overlapping interval of time;

an NFT processing module configured to generate a backpack NFT serving as a portable representation of a patient identity and to generate, for the health event, a compact NFT record associated with the backpack NFT, the compact NFT record comprising a token identifier, metadata associated with the health event, and a content-addressed hash of an off-chain patient-data payload, without storing protected health information of the off-chain patient-data payload on the blockchain; and wherein the NFT processing module utilizes a zero-knowledge proof protocol to assert that the metadata associated with the health event was generated from authenticated patient data according to the clinical-trial recordation rules without revealing underlying patient data to unauthorized entities; and an AI agent module configured to autonomously classify patient histories based on parameters identified in the clinical trial and create one or more cohorts of patients from the plurality of patients, by matching the parameters to metadata associated with compact NFT records in corresponding patient NFT series on the blockchain.

2. The patient health record system of claim 1, wherein the parameters comprise one or more of symptoms, responses, and dosage.

3. The patient health record system of claim 1, wherein each corresponding non-overlapping interval of time, and wherein the smart contract prevents patient data from the corresponding non-overlapping interval of time from being included in a second compact NFT record for a different interval of time.

4. The patient health record system of claim 1, wherein NFT data is recorded according to at least one of: ERC998, ERC6551 and ERC4337.

5. The patient health record system of claim 1, wherein a first wallet is created to store or control a private key associated with the compact NFT record.

6. The patient health record system of claim 1, wherein the content-addressed hash comprises an IPFS hash, decentralized-storage hash, or cryptographic hash recorded on the blockchain while the off-chain patient-data payload is stored in a secure off-chain storage facility.

7. The patient health record system of claim 1, wherein the metadata comprises one or more of a trial identifier, patient pseudonymous identifier, clinical-trial phase, event type, timestamp, trial location, dosage, response value, adverse-event indicator, efficacy endpoint, or outcome label.

8. The patient health record system of claim 1, wherein the attestation module records, on the blockchain, an attested hash associated with the off-chain patient-data payload and metadata identifying an attesting healthcare entity, provider, clinical research organization, or trusted third party.

9. The patient health record system of claim 1, wherein the zero-knowledge proof asserts that a cohort-generation rule was executed on authenticated clinical-trial data without revealing underlying patient data.

10. The patient health record system of claim 1, wherein the AI agent generates cohort metadata that is immutably recorded with or attached to one or more compact NFT records.

11. The patient health record system of claim 1, wherein the smart contract automatically retrieves or updates patient medical records from multiple healthcare providers and limits sharing of the records to authorized parties.

12. The patient health record system of claim 1, wherein the patient private key/wallet address pair is protected using biometric authentication, a hardware security module, a key management system, a multi-signature wallet, or a multi-party computation process.

13. The patient health record system of claim 4, wherein the compact NFT records are bound to a smart wallet or backpack token representing a clinical trial, healthcare provider, healthcare entity, or clinical research organization.

14. The patient health record system of claim 1, wherein the AI agent creates a cohort by matching metadata of compact NFT records to clinical-trial parameters without accessing the protected health information of the off-chain patient-data payload.

15. The patient health record system of claim 1, wherein the smart contract automates disclosure rules that reveal confidential patient data only to an authorized regulator while preserving patient privacy for other participants.

16. The patient health record system of claim 1, wherein the compact NFT record forms part of an auditable chain-of-custody for clinical-trial outcome data.

17. The patient health record system of claim 1, wherein the AI agent classifies patient histories based at least in part on metadata generated from authenticated health events recorded as a chronological series of compact NFT records.

* * * * *